United States Patent
Chan et al.

(10) Patent No.: US 12,295,699 B2
(45) Date of Patent: May 13, 2025

(54) MULTIPLE CEST CONTRAST IMAGING OF NOSE-TO-BRAIN DRUG DELIVERY USING CT-CONTRAST AGENT-LOADED LIPOSOMES

(71) Applicant: CITY UNIVERSITY OF HONG KONG, Kowloon (HK)

(72) Inventors: Wai Yan Chan, Kowloon (HK); Jianpan Huang, Kowloon (HK); Lok Hin Law, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 119 days.

(21) Appl. No.: 18/481,196

(22) Filed: Oct. 4, 2023

(65) Prior Publication Data
US 2024/0115136 A1      Apr. 11, 2024

Related U.S. Application Data

(60) Provisional application No. 63/413,137, filed on Oct. 4, 2022.

(51) Int. Cl.
| | | |
|---|---|---|
| *A61B 5/00* | (2006.01) | |
| *A61B 5/055* | (2006.01) | |
| *A61B 6/00* | (2006.01) | |
| *A61K 9/1271* | (2025.01) | |
| *A61K 49/04* | (2006.01) | |
| *A61M 11/00* | (2006.01) | |

(52) U.S. Cl.
CPC ............ *A61B 5/0042* (2013.01); *A61B 5/055* (2013.01); *A61B 6/481* (2013.01); *A61K 9/1271* (2013.01); *A61K 49/0438* (2013.01); *A61M 11/00* (2013.01)

(58) Field of Classification Search
CPC .................................................. A61B 5/0042
See application file for complete search history.

*Primary Examiner* — Joseph M Santos Rodriguez
(74) *Attorney, Agent, or Firm* — Conley Rose, P.C.; Michael W. Piper; Gayatry Nair

(57) ABSTRACT

Disclosed herein are methods for delivering a drug to the brain of a subject and monitoring the distribution of the drug therein. The method includes steps of: (a) intranasally administering of a first and second liposomes respectively loaded with the drug and a computed tomography (CT) contrast agent therein to the subject; (b) subjecting the brain of the subject of step (a) to a magnetic resonance imaging (MRI) scan; and (c) measuring chemical exchange saturation transfer (CEST) signals during the MRI scan in both olfactory bulb (OB) and frontal lobe (FL) regions at 1.2 ppm, 4.3 ppm, and −3.4 ppm, respectively.

13 Claims, 4 Drawing Sheets

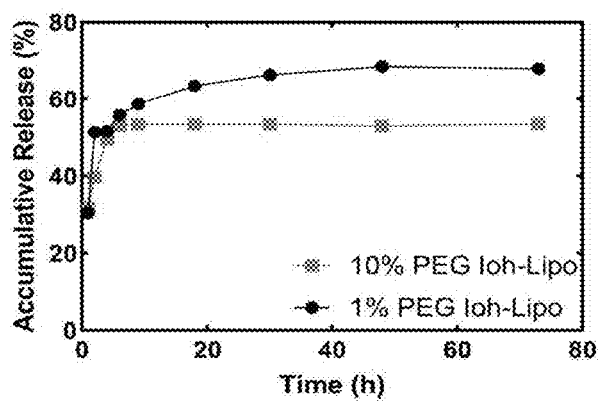
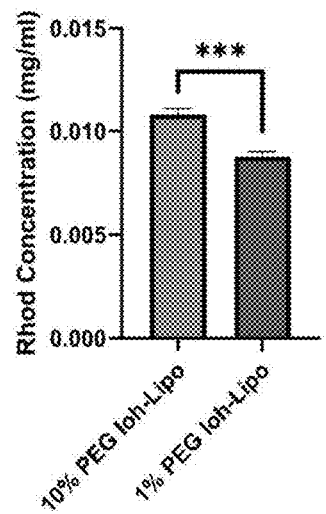
FIG. 1a
FIG. 1b
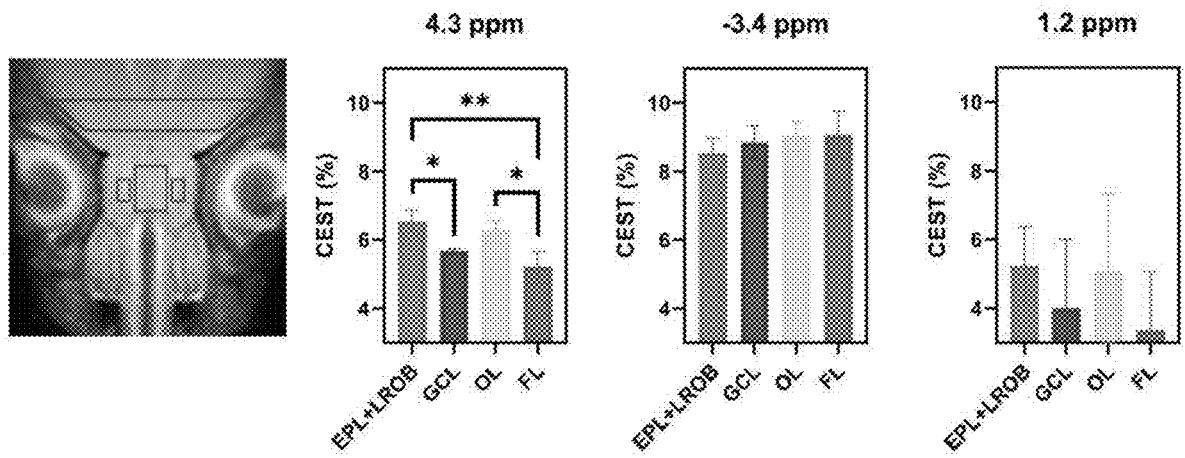
FIG. 5a
FIG. 5b
FIG. 5c
FIG. 5d

MULTIPLE CEST CONTRAST IMAGING OF NOSE-TO-BRAIN DRUG DELIVERY USING CT-CONTRAST AGENT-LOADED LIPOSOMES

CROSS-REFERENCE TO RELATED APPLICATIONS

This application claims priority to and the benefit of U.S. Provisional Patent Application No. 63/413,137, filed Oct. 4, 2022, the entirety of which is incorporated herein by reference.

BACKGROUND OF THE INVENTION

Field of the Invention

The present disclosure in general relates to the field of drug delivery and imaging, particularly, relates to novel methods of delivering a drug into the brain of a subject and monitoring the distribution of the drug in the brain non-invasively using magnetic resonance imaging (MRI).

Description of Related Art

Intranasal administration has been shown to be an effective way to deliver drugs to the brain via bypassing Blood Brain Barrier (BBB). US20080075671A1 discloses an intranasal drug, which is intranasally administering curcumin to the brain to treat Alzheimer's disease. Specifically, US20080075671A1 discloses intranasal administration of a curcumin containing pharmaceutical composition to an upper third of a nasal cavity of the mammal, wherein the curcumin is absorbed through a nasal mucosa and transported to the brain of the mammal. However, prior art such as US20080075671A1 does not show successful and efficient intranasal administration of mucus penetrable drug vehicles to treat various brain disease.

Accordingly, there exists in the related art a need of an improved methods and/or formulation for drug delivery in the brain. Such methods and/or formulations would be more efficient and easier-to-use compared to currently used technologies. Importantly, the improved methods and/or formulations should also allow the drugs to be tracked during and/or after the delivery non-invasively to refine the treatment.

SUMMARY OF THE INVENTION

The present disclosure provides novel methods of delivering a drug to the brain via intranasal administration and monitoring the distribution of the drug therein, e.g., in olfactory bulb (OB) and frontal lobe (FL) regions of the brain.

Accordingly, there is provided a method of delivering a drug to the brain of a subject and monitoring the distribution of the drug therein. The method comprises steps of:
(a) intranasally administering a first and second liposomes respectively loaded with the drug and a computed tomography (CT) contrast agent therein to the subject;
(b) subjecting the brain of the subject of step (a) to magnetic resonance imaging (MRI) scan; and
(c) measuring chemical exchange saturation transfer (CEST) signals during the MRI scan in both olfactory bulb (OB) and frontal lobe (FL) regions at 1.2 ppm, 4.3 ppm, and −3.4 ppm, respectively;
wherein,
each of the first and second liposomes in step (a) independently comprises a hydrophilic core; and a lipid bilayer shell formed by a cholesterol, and one or more of a phospholipid optionally modified with a polyethylene glycol (PEG), in which the PEG-modified phospholipid is arranged in the manner that the PEG are disposed outside the lipid bilayer shell, and the PEG is at least 7% by weight based on the total weight of the first or second liposomes;
the drug and the CT contrast agent are respectively disposed within the hydrophilic cores of the first and second liposomes; and
an increase in the CEST signals respectively measured at about 1.2 ppm, 4.3 ppm, and −3.4 ppm in step (c) represent the presence of the PEG, the CT contrast agent, and the phospholipid bilayer of the first or second liposomes in the OB and FL regions.

According to preferred embodiments of the present disclosure, in step (a), the first and second liposomes are intranasally administered to the subject at a ratio of 1:1 by volume.

Examples of the phospholipid suitable for forming the lipid bilayer shell of the present liposome include, but are not limited to, ceramide phosphorylcholine, ceramide phosphorylethanolamine, ceramide phosphoryllipid, 1,2-Distearoyl-sn-glycero-3-phosphocholine (DSPC), 1,2-Dipalmitoyl-sn-glycero-3-phosphocholine (DPPC), 1,2-dioleoyl-snglycero-3-phosphocholine (DOPC), 1,2-Distearoyl-sn-glycero-3-phosphoglycerol (DSPG), 1,2-Dipalmitoyl-sn-glycero-3-phosphoglycerol (DPPG), 1,2-Dioleoyl-sn-glycero-3-phosphoethanolamine (DOPE), 1,2-Distearoyl-sn-glycero-3-phosphoethanolamine (DSPE) 1,2-dioleoyl-3-trimethylammonium propane (DOTAP), 1,2-distearoyl-3-trimethylammonium propane (DSTAP), 1,2-dimyristoyl glycerol (DMG), phosphatidylethanolamine (PE), phosphatidylcholine (PC), phosphatidylserine (PS), phosphatidylinositol (PI), and phosphatidylglycerol (PG). In one preferred embodiment, the DSPE is modified with the PEG, and the lipid bilayer shell is formed by mixing the DSPC, the cholesterol, and the PEG-modified DSPE at a ratio of 50:40:10 by weight.

Examples of the drug suitable for use in the present method include, but are not limited to, a protein, a peptide, a small molecule drug (e.g., an anti-cancer drug or a neurodegenerative drug), an antibody, and a nucleic acid. In some examples, the first liposome is loaded with an anti-cancer drug, while the second liposome is loaded with CT contrast agent. Examples of anti-cancer drug suitable for use in the present method include, but are not limited to, cisplatin, carboplatin, oxaliplatin, cyclophosphamide, chlorambucil, ifosfamide, doxorubicin, gemcitabine, daunorubicin, valrubicin, idarubicin, vincristine, vinblastine, taxol, docetaxel, camptothecin (CPT), irinotecan (CPT-11), and topotecan (TPT).

In other examples, the first liposome is loaded with an antibody, while the second liposome is loaded with the CT contrast agent. Examples of antibody suitable for use in the present method include, but are not limited to, imatinib, gefitinib, erlotinib, cetuximab, panitumumab, zalutumumab, nimotuzumab, and matuzumab.

In further examples, the first liposome is loaded with a neurodegenerative drug, while the second liposome is loaded with the CT contrast agent. Examples of the neurodegenerative drug suitable for use in the present method include, but are not limited to, amantadine, apomorphine, baclofen, carbidopa, levodopa, dantrolene, donepezil, entacapone, galantamine, memantine, pramipexole, rasagiline, riluzole, rivastigmine, ropinirole, selegiline, tacrine, tetrabenazine, tizanidine, and tolcapone.

Examples of the CT contrast agent suitable for use in the present method include, but are not limited to, iohexol, ioxaglic acid, metrizamide, iopamidol, iopromide, iotrolan, ioversol, iopentol, iodixanol, iomeprol, iobitidiol, and ioxilan. In one preferred embodiment, the CT contrast agent is iohexol.

According to embodiments of the present disclosure, in step (a), the first and second liposomes are independently in the form of a drop, a spray, a mist, or a mixture thereof suitable for applied to the nasal or sinus passages of the subject.

In all embodiments of the present disclosure, the subject is a mammal, preferably, a human.

The details of one or more embodiments of this disclosure are set forth in the accompanying description below. Other features and advantages of the invention will be apparent from the detail descriptions, and from claims. It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where:

FIGS. 1(a)-1(b) show Release profiles and liposome retention properties of Ioh-Lipo with different PEG concentration. FIG. 1(a) Release profiles of 10% PEG and 1% PEG Ioh-Lipo, and FIG. 1(b) In vitro mucus retention study of 10% PEG and 1% PEG Ioh-Lipo with small size (<200 nm) (n=4). Comparisons were performed using one-way ANOVA. Differences were considered as statistically significant for P value<0.05 (*), P<0.01 (), and P<0.001 (*);

FIG. 2(a) Z-spectra and CEST spectra of Ioh-Lipo at FIG. 2(b) positive and FIG. 2(c) negative side, under $B_1$=0.6 μT and pH 7.0. $B_1$ power dependency of Ioh-Lipo CEST contrast at FIG. 2(d) 4.3 ppm, FIG. 2(e) 1.2 ppm and FIG. 2(f) −3.4 ppm;

FIGS. 5(a)-5(d) ROI analysis in different regions in the olfactory bulb and the frontal lobe. FIG. 5(a) T2w image with ROIs drawn for 4 different regions. ROI analysis at FIG. 5(b) 4.3 ppm, FIG. 5(c) at −3.4 ppm and FIG. 5(d) at 1.2 ppm. OB: olfactory bulb, FL (purple): frontal lobe, EPL+LROB (red): external plexiform layer+middle region between left and right OB, GCL (blue): granule cell layer, OL (green): olfactory limbus (OL) between OB and FL. Comparisons were made between the groups using one-way ANOVA. Differences were considered as statistically significant for P value<0.05 (*), P<0.01 (), and P<0.001 (*).

DETAILED DESCRIPTION OF THE PREFERRED EMBODIMENTS

Figure 2A:
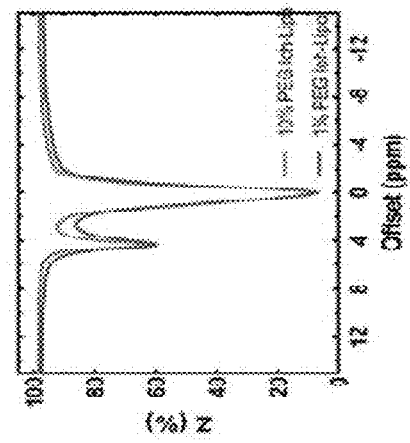
FIGS. 2(a)-2(f) show CEST properties of 10% PEG and 1% PEG Ioh-Lipo.

The detailed description provided below in connection with the appended drawings is intended as a description of the present disclosure and is not intended to represent the only forms in which the present disclosure may be constructed or utilized.

The following terms shall be interpreted according to the definitions set forth below. Terms not defined shall be interpreted according to the ordinary and standard usage in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

For the purposes of the present invention, liposomes mean particles formed with a hydrophilic nucleus, and a lipid outer shell optionally modified with a polyethylene glycol (PEG) (i.e., a Pegylated phospholipid bilayer) suitable for use in the present method, in which the liposomes containing molecules (e.g., drugs, CT contrast agents, and a combination thereof) are intranasally administered to the brain, thereby allowing effective doses of the encapsulated molecules in the liposomes are transferred to the brain. The molecules encapsulated within the liposomes are effective for their intended purpose (e.g., for the treatment and/or prophylaxis of diseases, and/or for monitoring the distribution of liposomes in the brain) once they are taken up into the brain cells.

As used herein, the term "contrast agent" refers to substances used to enhance the visibility of internal structures in X-ray based imaging techniques, such as computed tomography (CT). In the present disclosure, the contrast agents absorb external X-rays, thereby allowing a liposome containing the contrast agents therein to be tracked during imaging, such as during CT scan, magnetic resonance imaging (MRI) and the like.

As used herein, the term "intranasal administration" or "nasal application" as used herein means applied through the nose into the nasal or sinus passages or both. The administration may be achieved by drops, sprays, mists, coating or mixtures thereof applied to the nasal or sinus passages.

As used herein, the term "subject" refers to any animal including, but not limited to, humans, non-human primates, rodents, and the like, to which the liposomes and methods of the present disclosure are administered. Typically, the term "subject" as used herein refers to a human subject.

Provided herein is a method for delivering a drug to the brain of an individual and monitoring the distribution of the drug in situ by delivering a first and second liposomes to the brain through nasal application. The first liposome is loaded with the drug, while the second liposome is loaded with a contrast agent, preferably, a CT contrast agent. The present method demonstrates that a speedier and more efficient absorption of a drug molecule and a CT contrast agent to the brain is realized by intranasal administration. The present method thus may be useful for delivering drug molecules along with CT contrast agents in the treatment and/or prophylaxis of brain diseases such as brain tumors, neurodegenerative diseases (e.g., Alzheimer's disease, Parkinson's disease, and etc.), epilepsy, and the like; while monitoring the distribution of the drug molecules in the brain.

The present method includes steps of:
(a) intranasally administering a first and second liposomes respectively loaded with the drug and a computed tomography (CT) contrast agent therein to the subject;
(b) subjecting the brain of the subject of step (a) to a magnetic resonance imaging (MRI) scan; and
(c) measuring chemical exchange saturation transfer (CEST) signals during the MRI scan in both olfactory bulb (OB) and frontal lobe (FL) regions at 1.2 ppm, 4.3 ppm, and −3.4 ppm, respectively;
wherein,
each of the first and second liposomes in step (a) independently comprises a hydrophilic core; and a lipid bilayer shell formed by a cholesterol, and one or more of a phospholipid optionally modified with a polyethylene glycol (PEG), in which the PEG-modified phospholipid is arranged in the manner that the PEG are disposed outside the lipid bilayer shell, and the PEG is at least 7% by weight based on the total weight of the first or second liposomes;
the drug and the CT contrast agent are respectively disposed within the hydrophilic cores of the first and second liposomes; and
an increase in the CEST signals respectively measured at about 1.2 ppm, 4.3 ppm, and −3.4 ppm in step (c) represent the presence of the PEG, the CT contrast agent, and the phospholipid bilayer of the first or second liposomes in the OB and FL regions.

As defined above, liposomes are particles formed with a hydrophilic nucleus, and a lipid outer shell optionally modified with a polyethylene glycol (PEG). The lipid outer shell is formed by mixing proper amounts of phospholipid, cholesterol, and PEG-modified phospholipids in an aqueous media, in which the phospholipids, the cholesterol and the PEG-modified phospholipids self-assemble into the lipid bilayer. Examples of the phospholipid suitable for forming the lipid bilayer shell of the present liposome include, but are not limited to, ceramide phosphorylcholine, ceramide phosphorylethanolamine, ceramide phosphoryllipid, 1,2-Distearoyl-sn-glycero-3-phosphocholine (DSPC), 1,2-Dipalmitoyl-sn-glycero-3-phosphocholine (DPPC), 1,2-dioleoyl-snglycero-3-phosphocholine (DOPC), 1,2-Distearoyl-sn-glycero-3-phosphoglycerol (DSPG), 1,2-Dipalmitoyl-sn-glycero-3-phosphoglycerol (DPPG), 1,2-Dioleoyl-sn-glycero-3-phosphoethanolamine (DOPE), 1,2-Distearoyl-sn-glycero-3-phosphoethanolamine (DSPE) 1,2-dioleoyl-3-trimethylammonium propane (DOTAP), 1,2-distearoyl-3-trimethylammonium propane (DSTAP), 1,2-dimyristoyl glycerol (DMG), phosphatidylethanolamine (PE), phosphatidylcholine (PC), phosphatidylserine (PS), phosphatidylinositol (PI), and phosphatidylglycerol (PG). In one preferred embodiment, the DSPE is modified with the PEG, and the lipid bilayer shell is formed by mixing the DSPC, the cholesterol, and the PEG-modified DSPE at a weight ratio of 50:40:10. Preferably, after self-assembling, the PEG-modified phospholipid is arranged in the manner that the PEG are disposed outside the lipid bilayer shell. According to further embodiments of the present disclosure, the PEG is at least 7% by weight based on the total weight of the liposome, such as 7%, 8%, 9%, and 10% by weight; preferably, the PEG is at least 8% by weight based on the total weight of the liposome; more preferably, the PEG is at least 9% by weight based on the total weight of the liposome; and most preferably, the PEG is at least 10% by weight based on the total weight of the liposome.

For the purposes of the present invention, the first liposome is loaded with desired drug molecules, while the second liposome is loaded with CT agents. Preferably, drug molecules and CT agents are independently mixed with afore-mentioned lipid mixtures (i.e., phospholipid, cholesterol, and PEG-modified phospholipids) during the lipid bilayer formation process, thereby are automatically encapsulated within the hydrophilic core of the liposome after self-assembling of the lipid bilayer. Examples of the drug molecule suitable for use in the present method include, but are not limited to, a protein, a peptide, a small molecule drug (e.g., an anti-cancer drug, a neurodegenerative drug, and the like), an antibody, a nucleic acid, and the like. The drug molecules suitable for use in the present method are those suitable for treating brain tumors, neurodegenerative diseases (e.g., Alzheimer's disease, Parkinson's disease, and etc.), epilepsy, and the like. In some examples, the first liposome is loaded with anti-cancer drug, while the second liposome is loaded with CT contrast agent. Examples of anti-cancer drug suitable for use in the present method include, but are not limited to, cisplatin, carboplatin, oxaliplatin, cyclophosphamide, chlorambucil, ifosfamide, doxorubicin, gemcitabine, daunorubicin, valrubicin, idarubicin, vincristine, vinblastine, taxol, docetaxel, camptothecin (CPT), irinotecan (CPT-11), and topotecan (TPT). In other examples, the first liposome is loaded with an antibody, while the second liposome is loaded with and CT contrast agent. Examples of antibody suitable for use in the present method include, but are not limited to, imatinib, gefitinib, erlotinib, cetuximab, panitumumab, zalutumumab, nimotuzumab, and matuzumab.

In further examples, the first liposome is loaded with a neurodegenerative drug, while the second liposome is loaded with the CT agent. Examples of the neurodegenerative drug suitable for use in the present method include, but are not limited to, amantadine, apomorphine, baclofen, carbidopa, levodopa, dantrolene, donepezil, entacapone, galantamine, memantine, pramipexole, rasagiline, riluzole, rivastigmine, ropinirole, selegiline, tacrine, tetrabenazine, tizanidine, and tolcapone.

Examples of the CT contrast agent suitable for use in the present method include, but are not limited to, iohexol, ioxaglic acid, metrizamide, iopamidol, iopromide, iotrolan, ioversol, iopentol, iodixanol, iomeprol, iobitidiol, and ioxilan. In one preferred embodiment, the CT contrast agent is iohexol.

According to embodiments of the present disclosure, each of the first and second liposomes of the present disclosure is less than 250 nm in diameter, such as 245 nm, 240 nm, 235 nm, 230 nm, 225 nm, 220 nm, 215 nm, 210 nm, 205 nm, 200 nm, 195 nm, 190 nm, 185 nm, 180 nm, 175 nm, 170 nm, 165 nm, 160 nm, 155 nm, and 150 nm; preferably, less than 200 nm in diameter, such as 195 nm, 190 nm, 185 nm, 180 nm, 175 nm, 170 nm, 165 nm, 160 nm, 155 nm, and 150 nm; more preferably, less than 170 nm in diameter, such as 165 nm, 160 nm, 155 nm, and 150 nm. According to preferred embodiments of the present disclosure, each of the first or second liposomes is about 166 nm in diameter.

According to embodiments of the present disclosure, the present liposomes are formulated into drops, sprays, mists, coating or mixtures thereof suitable for nasal application. Specifically, the formulated drops, sprays, mists, coating or mixtures thereof are applied to the nasal or sinus passages or both of the subject, and eventually cross the blood-brain barrier (BBB) and are taken up by the brain cells.

To confirm whether the liposome containing formulation has indeed reached the brain, the subject is subjected to a magnetic resonance imaging (MRI) scan (step (c)), and chemical exchange saturation transfer (CEST) signals during the MRI scan are measured (step (d)). According to embodiments of the present disclosure, CEST signals at −3.4 ppm originated from the liposomes, CEST signals at 1.2 ppm are contributed by the PEG molecules, and CEST signals at 4.3 ppm are from the CT contrast agent (i.e., iohexol). Accordingly, CEST signals at about −3.4 ppm. 1.2 ppm, and 4.3 ppm are used as indications for the presence or absence of the present liposomes in the brain. According to preferred embodiments of the present disclosure, an increase in CEST signals respectively at 1.2 ppm, 4.3 ppm, and −3.4 ppm represent the presence of the PEG, the CT contrast agent, and the phospholipid bilayer of the liposome in the OB and FL regions of the brain.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
CT contrast agent solution preparation

Briefly, 700 ul Iohexol solution (647 mg/ml or 787.9 mM) was dissolved in 500 ul distilled water in pH 7.0 to produce an Iohexol solution in the concentration of 459.6 mM.

Iohexol-Loaded Liposome Preparation

Iohexol encapsulated liposome (Ioh-Lipo) was prepared through thin film hydration, and extrusion method using a formulation of DSPC:cholesterol:DSPE-PEG-2000:rhodamine=50:40:10:0.18 for 10% PEG Ioh-Lipo, and 55:44:1: 0.18 for 1% PEG Ioh-Lipo. Lipid mixture was dissolved in chloroform and evaporated to form a dry homogeneous thin film layer by a rotary evaporator (Heidolph, Schwabach, Germany). The lipid film was then rehydrated with the CT contrast agents (500 ul of Iohexol with 700 ul distilled water) with temperature higher than the transition temperature of the lipid, and sonicated for 30 min to form large multilamellar liposomes (MLVs). The solution was finally extruded through 400 nm polycarbonate membranes for 15 times then through 200 nm polycarbonate membranes for another 15 times to obtain the resultant liposome. The unloaded drug of the resultant liposome solution was filtered through Sephadex G-50 gel columns twice before imaging.

Liposome Characterization

The size, polydispersity index (PDI) and surface charge of liposomes were measured by dynamic light scattering (DLS) at room temperature by Zetasizer (Malvern Instruments, UK). Particle concentration was measured by Nanosight (Malvern Instruments, UK).

Iohexol Release Study

The loading of Iohexol in liposomes was estimated by measuring the UV absorbance at 245 nm using UV-VIS spectrometer (PerkinElmer, MA, USA). Ioh-Lipo were treated with Triton X-100 solution to completely release the Iohexol payload, diluted to proper concentration, followed by UV measurements. The concentration was then determined by the calibration curves of Iohexol solutions with known concentrations. Iohexol release from liposomes was studied using a dialysis method. Dialysis bags were soaked before use in distilled water at room temperature for 12 h to remove the preservative, followed by rinsing thoroughly in distilled water. The release experiments were done immediately after the preparation of liposomes. The liposome stock solution was diluted 10 times. The resulting liposomes suspension 500 µl was taken to dialysis bag (cut off molecular weight: 3000/5000) and immersed into 10 mL PBS solution. The sac was hung inside a conical flask with the help of a glass rod so that the portion of the dialysis with the formulation dipped into the buffer solution. The flask was kept on a magnetic stirrer and stirring was maintained at 100 rp at 37° with a thermostatic control. At predetermined time point, 2 mL supernatant was taken out and re-supplemented with fresh PBS, followed by UV measurements.

$^1$H NMR Experiment

A weighted sample of dried 10% PEG Ioh-Lipo or 1% PEG Ioh-Lipo (30 mg) was dissolved in $D_2O$. An aliquot of sample (500 µL) was placed into a 5-mm NMR tube. Spectra (0-10 ppm) were acquired by Bruker 400 MHz "AVANCE III" Nuclear Magnetic Resonance System (NMR-400) (Bruker, Ettlingen, Germany). Chemical shifts of Iohexol were at 3.89 ppm (C—OH), and PEG backbone at 3.54 ppm. Integrals at 3.54 ppm were used to calculate the PEG content.

Cell Preparation and Mucus Penetration Study

Human nasal epithelial cell RPMI 2650 cells were used for liposome retention cell study. The cells were seeded in 12-wells-plate and maintained in DMEM supplemented with 10% FBS and 1% Penicillin-Streptomycin. The cell cultures were maintained at 37° C. in a >95% humidified atmosphere of 5% $CO_2$ in air with media changes on alternate days. The cell is maintained for 14 days after 100% confluent for mucus secretion. 10% PEG Ioh-Lipo and 1% PEG Ioh-Lipo were diluted with the cell culture media and added in each well for 30 mins. The liposome mixture in the culture plate is extracted and washed by PBS before measuring the fluorescence reading by microplate reader (Molecular Devices, CA, USA)

In Vitro CEST MRI Measurement

In-vitro MRI images for phantom experiments of drug solutions and drug encapsulated liposome were acquired on a horizontal bore 3 T Bruker BioSpec system (Bruker, Ettlingen, Germany) equipped with a 40-mm volume transceiver coil. The CEST sequence was rapid acquisition with relaxation enhancement (RARE) sequence with a continuous wave (CW) pre-saturation module. The parameters were set as following: slice thickness=2 mm, field of view (FOV) =26×24/30×9 mm$^2$ for the Iohexol solution/Ioh-Lipo phantom, image size=32×32, RARE factor=32, repetition time/echo time (TR/TE)=6000/77 ms. saturation power (B1) was varied as: 0.6, 0.8, 0.9, 1.0, 1.2, 1.4 µT, saturation time (tsat)=3 s, CEST frequency varied from −15 to +15 ppm, with a step of 0.2 ppm between −6 to 6 ppm, a step of 1 ppm between ±6 and ±15 ppm and extra acquisition points on ±2.1, ±2.25, ±2.3, ±2.35, ±2.45, ±2.5, ±4.1, ±4.25, ±4.3, ±4.35, ±4.5 ppm and ±20 ppm. Three M0 images at 200 pp were acquired for normalization. Thus, the total scan time of a CEST acquisition was 10 min 36 s.

Animal Preparation

The Animal Ethics Committee and the Institutional Laboratory Animal Research Unit of City University of Hong Kong approved all animal experiments and animal registration in this study. All animals were housed under standard laboratory conditions, with access to food and water. Six 12-weeks-old ICR mice are used for intranasal administration of CT agents loaded liposome. 150 ul of liposomal solution was administrated intranasally to one side of the nasal cavity by pipette into the ICR mouse.

In Vivo MRI

T2-weighted (T2w) and CEST images were acquired pre-injection and 0.5, 1 and 1.5 h after intranasal injection of Ioh-Lipo. Treated mouse was hold for 30 mins to ensure liposomes were transported and penetrated into the olfactory bulb. The in-vivo MRI images for intranasal administration experiments at the olfactory bulb of mice were acquired on a horizontal bore 3 T Bruker BioSpec system (Bruker, Ettlingen, Germany) equipped with one 82 mm quadrature volume resonator as a transmitter and a single surface coil as a receiver. The T2 weighted image and CEST data in axial view were acquired. The CEST sequence was RARE sequence with a CW pre-saturation module. The parameters were set as followings: slice thickness=2 mm, field of view (FOV)=16×16 mm$^2$, image size=64×64, RARE factor=32, TR/TE=5000/5 ms. B1 was varied as: 0.6, 0.9 µT, tsat=3 s, CEST frequency varied from −15 to +15 ppm, with a step of 0.2 ppm between −6 to 6 ppm, a step of 1 ppm between ±6 and ±15 ppm and extra acquisition points on ±2.1, ±2.25, ±2.3, ±2.35, ±2.45, ±2.5, ±4.1, ±4.25, ±4.3, ±4.35, ±4.5 ppm and ±20 ppm. Three M0 images at 200 ppm were acquired for normalization. Thus, the total scan time of a CEST acquisition was 14 min 10 s.

Data Analysis

The data were processed by custom-written MatLab (Mathworks, Natick, MA) code. After acquiring CEST data, the raw Z-spectra (Z) were formed by:

$$Z(\Delta\omega) = \frac{S_{sat}(\Delta\omega)}{S_o} \quad (1)$$

where $\Delta$ presented the frequency offsets, while $S_{sat}(\Delta\omega)$ and $S_o$ were the magnetization signals with saturation and without saturation, respectively. After the raw Z-spectra formation, the B0 correction was performed on a pixel-wise basis. Lorentzian difference analysis was adopted for calculating CEST contrasts. The Lorentzian line shape function is expressed as:

$$L_i(\Delta\omega) = \frac{A_i}{1 + \left[\frac{\Delta\omega - \delta_i}{\gamma_i/2}\right]^2} \quad (2)$$

where Ai represented the peak amplitude, Γi represented the full-width-at-half-maximum and di represented the peak position. The di was set to 0 ppm for DS and −2.5 ppm for MT as the B0 was corrected. The Z-spectrum data from −0.8 ppm to 0.8 ppm and from ±10 ppm to ±20 ppm was used for the fitting of reference curve ($Z_{ref}$). For the in vitro phantom data, DS effect was fitted to obtain $Z_{ref}$:

$$Z_{ref}(\Delta\omega)=1-L_{DS}(\Delta\omega) \quad (3)$$

For the in vivo data, both DS and MT effects were fitted to obtain $Z_{ref}$:

$$Z_{ref}(\Delta\omega)=1-L_{DS}(\Delta\omega)-L_{MT}(\Delta\omega) \quad (4)$$

The CEST contrast (%) was quantified by subtracting the Z-spectrum from the fitted reference curve:

$$CEST(\Delta\omega)=[Z_{ref}(\Delta\omega)-Z(\Delta\omega)]\times100\% \quad (5)$$

Histology

After MRI, mice were deeply anesthetized with 2% isoflurane gas and then intracardially perfused with phosphate-buffered saline (PBS). Whole brains were harvested and fixed in formalin and dehydrate in sucrose before cryosectioning. Axial slices at 20-µm thickness were sectioned and mounted. Liposomal distribution in the brain sections were detected by the rhodamine decorated liposomes, and the nuclei were stained by DAPI. The Axial brain sections were imaged with Leica TCS SP8 confocal microscopy system (Leica Microsystem, Germany).

Example 1 Characterization of the Present Liposomes Loaded with Drug and CT Contrast Agent 1.1 CEST Characterization of CT Contrast Agents CEST properties of Iohexol solution was firstly examined in vitro. The Iohexol (n=3) at 459.6 mM and pH 7.0 showed strong CEST contrast at 4.3 ppm for all investigated $B_1$ powers. The CEST contrast increased from 35.2±0.1% to 61.7±0.1% when the $B_1$ power increased from 0.6 µT to 1.4 µT (data not shown). This indicated that Iohexol could be sensitively detected by CEST MRI even at a low power (0.6 µT) at low field strength (3 T). The CEST contrast increased linearly from 8.5±0.2% to 33.7±0.1% ($R^2$=0.9974) when the concentration of Iohexol solution increased from 98.4 mM to 459.6 mM (data not shown).

1.2 Characterization of Iohexol Loaded Liposomes (Ioh-Lipo)

Two liposome formulations, i.e., Ioh-Lipo with 10% PEG and 1% PEG, were investigated in this example. The properties of liposomes, including particle size, polydispersity index (PDI), zeta potential and particle concentration were analyzed, and results are summarized in Table 1.

TABLE 1

Characterization of Ioh-Lipo with different PEG concentration (n = 3)

| Liposome | Concentration (Particles/mL) | Size (nm) | PDI | Zeta Potential (mV) |
|---|---|---|---|---|
| 10% PEG | 3.67 × 10$^{16}$ | 166.3 ± 0.7 | 0.2 ± 0.02 | −6.8 ± 0.07 |

TABLE 1-continued

Characterization of Ioh-Lipo with different PEG concentration (n = 3)

| Liposome | Concentration (Particles/mL) | Size (nm) | PDI | Zeta Potential (mV) |
|---|---|---|---|---|
| Ioh-Lipo 1% PEG Ioh-Lipo | $5.90 \times 10^{16}$ | 173.9 ± 0.4 | 0.2 ± 0.01 | −4.4 ± 0.40 |

It was found that the 10% PEG Iohexol loaded liposome (n=3) had a particle size of 166.3±1.5 nm, PDI of 0.2±0.02 and zeta potential of −6.8±0.07 mV. At a comparable particle concentration, the 1% PEG Iohexol loaded liposome (n=3) had a particle size of 173.9±0.4 nm, PDI of 0.2±0.01 and zeta potential of −4.4±0.04 mV. Further, NMR data confirmed that the PEG content was >10 times higher in 10% PEG Ioh-Lipo than that in 1% PEG Ioh-Lipo, where peak at 3.5 ppm indicated the presence of PEG and peaks at 3.2-4.0 ppm indicated the presence of Iohexol.

1.2.1 Release Profile and In Vitro Mucus Retention Study

The release profiles for both 10% PEG Ioh-Lipo and 1% PEG Ioh-Lipo were monitored for 3 days, results are depicted in FIG. 1a. It was found that for 10% PEG Ioh-Lipo, 31.7% of its content was release after 1 hour and the release reached a plateau at around 9 hrs. The maximum accumulative release for 10% PEG Ioh-Lipo was up to 53.5% after 73 hr. As to 1% PEG Ioh-Lipo, 30.3% was released after 1 hour and the release reached the plateau at around 30 hr. The maximum accumulative release was up to 68.5% after 48 hr.

The mucus retention study was investigated using RPMI 2650 cells, which were reported to have sufficient mucus. Accordingly, rhodamine labeled liposomes with either 10% PEG or 1% PEG Ioh-Lipo were applied onto the RPMI cells that have been cultured for 14 days. After 30 min of incubation, fluorescence reading was recorded to examine the mucus retention differences between 10% PEG and 1% PEG Ioh-Lipo in the mucus of the cells. A 20% higher retention in the mucus of RPMI 2650 cells was observed in cells treated with 10% PEG Ioh-Lipo than with 1% PEG Ioh-Lipo (FIG. 1b, 0.011±0.0001 mg/ml vs. 0.009±0.0001 mg/ml, P<0.001).

1.2.3 CEST Characterization of Iohexol Loaded Liposomes

Figure 2B:
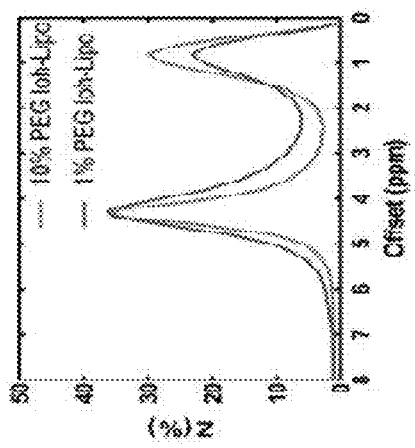
Figure 2C:
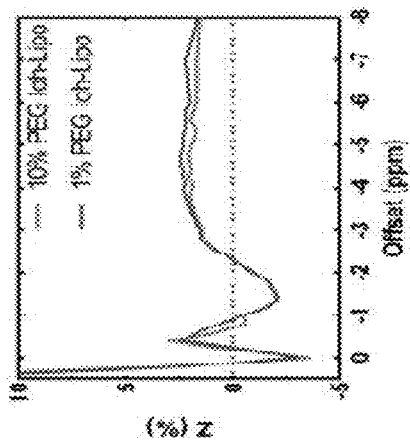
Figure 2D:
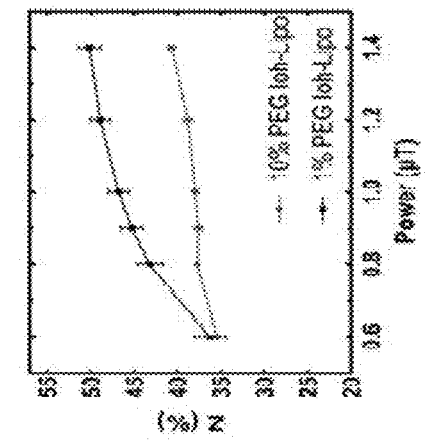
Figure 2E:
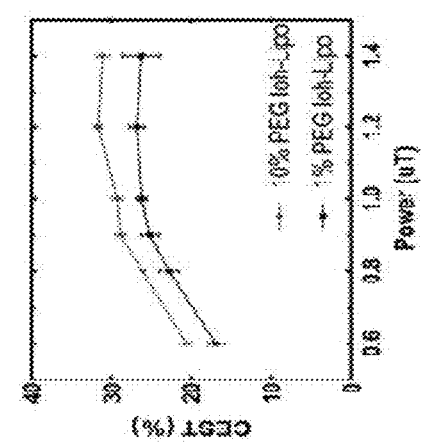
Figure 2F:
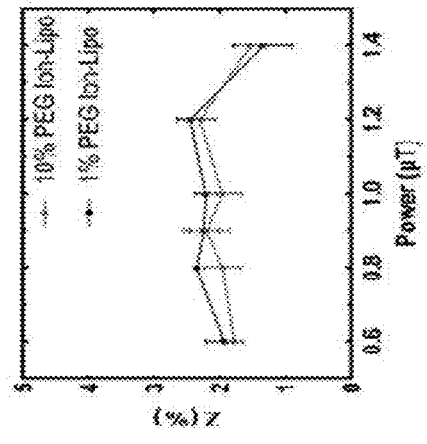

CEST properties of Ioh-Lipo were first examined in vitro. As shown in FIG. 2, both formulations of Ioh-Lipo (n=3) showed high CEST contrast at 4.3 ppm (FIG. 2b), 35.4±0.18% for 10% PEG Ioh-Lipo and 36.2±1.06% for 1% PEG Ioh-Lipo; and comparable CEST contrast at −3.4 ppm (FIG. 2c), 1.8±0.07% for 10% PEG Ioh-Lipo and 1.9±0.16% for 1% PEG Ioh-Lipo at a B1 power of 0.6 µT; CEST contrast at 1.2 ppm was 20.6±0.4% for 10% PEG Ioh-Lipo and 16.9±0.6% % for 1% PEG Ioh-Lipo. CEST contrast was acquired at a series of $B_1$ from 0.6 µT to 1.4 µT for optimization. At both 4.3 ppm and 1.2 ppm, CEST contrast increased as the $B_1$ power increased (FIG. 2d, e), which were relatively linear at 0.6-0.9 µT. The CEST contrast at −3.4 ppm of both 10% PEG Ioh-Lipo and 1% PEG Ioh-Lipo were at around 2% when the $B_1$ power increased from 0.6 µT to 1.2 µT, and was much lower at 1.4 µT (FIG. 2f).

1.2.4 In Vivo CEST MRI

Mice received 150 µl of either 10% PEG Ioh-Lipo (n=4) or 1% PEG Ioh-Lipo (n=4) intranasally were imaged. T2-weighted (T2w) and CEST images were acquired pre-injection and 0.5, 1, 1.5 hr after injection. In the considerations of other contributions to the z-spectrum in vivo, among the optimized $B_1$ in vitro (FIG. 2, d-f), we compared the CEST contrast in OB at $B_1$ of 0.6 µT and 0.9 µT. It was found that a low saturation power could avoid large contaminations from direct water saturation (DS) and magnetization transfer (MT) (data not shown). Thus, Z-spectra were acquired using a $B_1$ power of 0.6 uT in vivo, which provided comparable CEST contrasts for 10% PEG and 1% PEG Ioh-Lipo in vitro (FIG. 2). CEST contrasts at 4.3 ppm, −3.4 ppm and 1.2 ppm were obtained from OB and FL (FIGS. 3, 4). It was found that in the cohort received 10% PEG Ioh-Lipo, CEST contrast increased by 76.9±30.4% at 4.3 ppm and 11.4±2.1% at −3.4 ppm in OB at 0.5 hr after injection compared to pre-injection. Meanwhile, CEST contrast increased by 50.2±16.3% at 4.3 ppm and 8.2±2.9% at −3.4 ppm in FL. Interestingly, we also observed a CEST contrast enhancement at around 1.2 ppm (increased by 35.4±24.9% in OB and 56.0±23.5% in FL, 0.5 h after injection), which could be contributed by the hydroxyl protons of Iohexol and the higher PEG content of the 10% PEG Ioh-Lipo formulation (FIG. 2b).

Figures 3A, 3B, 3C, 3D, 3E, 3F:
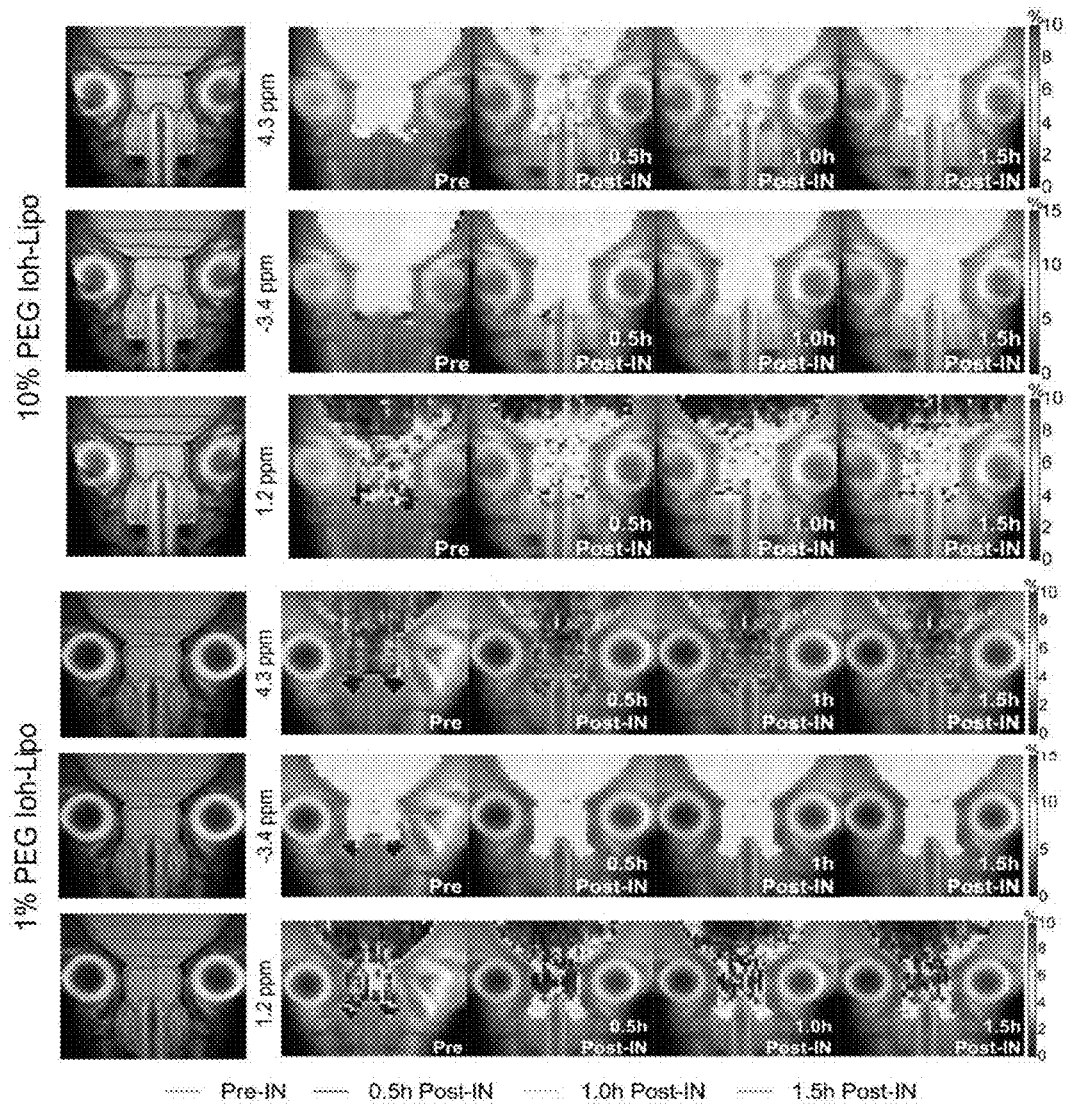
FIGS. 3(a)-3(f) In vivo experiment of intranasal administration of Ioh-Lipo in mice. T2w image and CEST maps (4.3 ppm, −3.4 ppm and 1.2 ppm) at pre-injection, and 0.5, 1, 1.5 h after injection, for FIG. 3(a) 10% PEG Ioh-Lipo and FIG. 3(b) 1% PEG Ioh-Lipo. Z-spectra and CEST spectra for 10% PEG Ioh-Lipo of FIG. 3(c) OB and FIG. 3(d) FL. Z-spectra and CEST spectra for 1% PEG Ioh-Lipo of FIG. 3(e) OB and FIG. 3(f) FL.
Figure 4A:
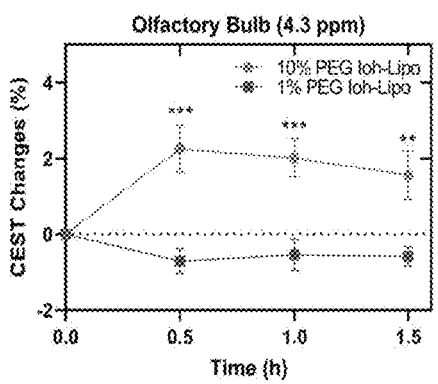
FIGS. 4(a)-4(f) CEST signal changes after intranasal administration of different PEG concentration Ioh-Lipo in frontal lobe and olfactory bulb. CEST signal changes in OB FIG. 4(a) at 4.3 ppm, FIG. 4(c) −3.4 ppm and FIG. 4(e) 1.2 ppm. CEST signal changes in FL FIG. 4(b) at 4.3 ppm, FIG. 4(d) at −3.4 ppm and FIG. 4(f) at 1.2 ppm. Comparisons were made between the groups using multiple t test. Differences were considered as statistically significant for P value<0.05 (*), P<0.01 (), and P<0.001 (*)
Figure 4B:
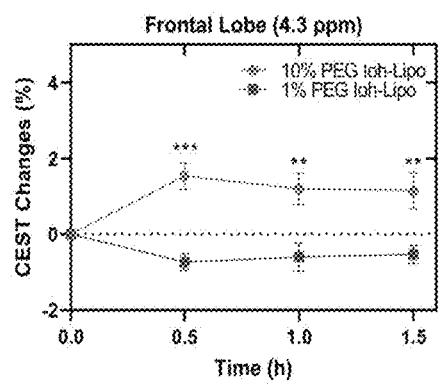
Figure 4C:
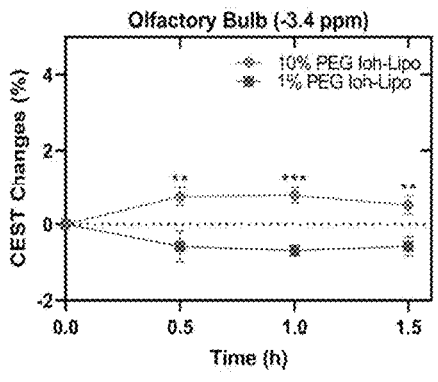
Figure 4D:
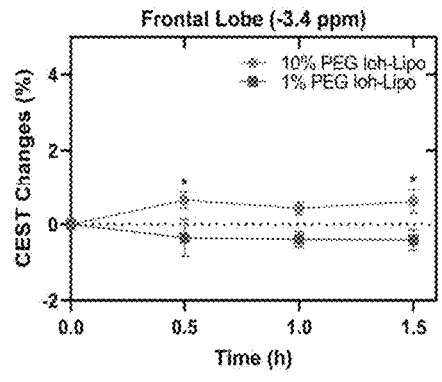
Figure 4E:
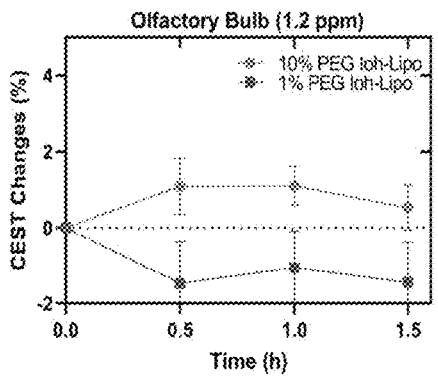
Figure 4F:
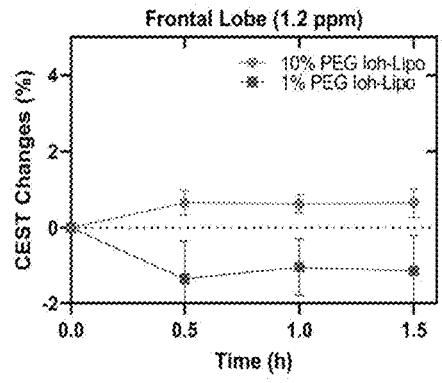

In contrast, mice received 1% PEG Ioh-Lipo did not show significant changes at 4.3 ppm, −3.4 and 1.2 ppm over the period of imaging (FIGS. 3 and 4). Distinctive peak at 4.3 ppm was consistently observed in 10% PEG Ioh-Lipo spectra (FIG. 3c, 3d) but not in 1% PEG Ioh-Lipo spectra (FIG. 3e, 3f). Moreover, it was also found that mice received 10% PEG Ioh-Lipo with size >200 nm also did not show significant changes at 4.3, −3.4 and 1.2 ppm after injection (data not shown).

Notably, we observed different regional changes of CEST contrasts at 4.3 ppm, −3.4 ppm and 1.2 ppm in OB and FL among these CEST maps of 10% PEG Ioh-Lipo (FIG. 3a). Both CEST contrasts at 4.3 ppm and −3.4 ppm of 10% PEG Ioh-Lipo were significantly higher than that of 1% PEG Ioh-Lipo (FIG. 4a-4d, P<0.001; P<0.001; P<0.05; P<0.01, respectively) at 0.5 hr after injection. CEST contrast differences were 3.0% at 4.3 ppm and 1.3% at −3.4 ppm in the Oft while 2.3% at 4.3 ppm and 1.0% at −3.4 ppm in the FL. For 10% PEG Ioh-Lipo, OB and FL increased by a similar percentage (11.4±2.1% vs. 8.2±2.9%) at −3.4 ppm, while OB increased more than FL at 4.3 ppm (76.9±30.4% vs. 50.2±16.3%)

Based on these observations, we further analyzed the CEST signal changes in small regions, such as external plexiform layer (EPL), middle region between left and right OB (LROB), granule cell layer (GCL) and olfactory limbus (OL) between OB and FL (FIG. 3a) in 10% PEG Ioh-Lipo cohort for analyzing the distribution of Iohexol and liposome in the brain. We compared CEST contrast at 4.3 ppm, −3.4 ppm and 1.2 ppm at 0.5 h after injection (FIG. 5b-5d). With the consideration of spatial resolution limitation, EPL and LROB were combined (EPL+LROB). At 4.3 ppm, the CEST contrast of EPL+LROB and OL were significantly higher than that of GCL and FL (P<0.05). OL (5.2±0.26% vs. 6.3±0.16%, P=0.012) and EPL+LROB (5.2±0.26% vs. 6.5±0.19%, P=0.004), were significantly higher than that of FL, which was slightly lower than that of GCL (5.2±0.26% vs. 5.7±0.04%). Among all investigated ROIs, EPL+LROB showed the highest CEST contrast which was significantly higher than that of GCL (5.7±0.04%, P=0.039). EPL+LROB also had the highest contrast at both 4.3 ppm and 1.2 ppm, although no significant difference at −3.4 ppm and 1.2 ppm among all ROIs (FIG. 5c, 5d).

The distribution of liposomes was validated by histology via the rhodamine labels on liposomes. Rhodamine (red) indicated the distribution of rhodamine-labeled liposomes and DAPI (blue) was the counter stain for nuclei. The DAPI signal was comparable for mice received 10% PEG and 1% PEG Ioh-Lipo injections. Mice received 10% PEG Ioh-Lipo showed obviously higher distribution of rhodamine-labeled liposomes in both FL and OB compared to the mice received 1% PEG Ioh-Lipo (data not shown). Notably, strong rhodamine signal was observed in specific regions including EPL+LROB, GCL, OL and FL (data not shown). These observations echoed the MRI findings (FIGS. 3-5), thus confirming the contributions of Ioh-Lipo to CEST contrasts after intranasal administration in vivo.

Taken together, the findings demonstrated that CT contrast agent (i.e., Iohexol) loaded liposomes with >10% PEG enables the imaging of nose-to-brain delivery using multiple CEST contrast. Iohexol has amide protons, which generated strong CEST contrast at 4.3 ppm (FIG. 1). After being loaded into liposome (Ioh-Lipo), the CEST contrast at 4.3 ppm remained high (at 35%, $B_1$=0.6 µT). Moreover, additional CEST contrast of 1.8% at −3.4 ppm and 20.6% at 1.2 ppm were observed in Ioh-Lipo (FIG. 2), which can be used to indicate liposome distribution after administration.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of delivering a drug to the brain of a subject and monitoring the distribution of the drug therein comprising:
   (a) intranasally administering a first and second liposomes respectively loaded with the drug and a computed tomography (CT) contrast agent therein to the subject;
   (b) subjecting the brain of the subject of step (a) to a magnetic resonance imaging (MRI) scan; and
   (c) measuring chemical exchange saturation transfer (CEST) signals during the MRI scan in both olfactory bulb (OB) and frontal lobe (FL) regions at 1.2 ppm, 4.3 ppm, and −3.4 ppm, respectively;
   wherein,
   each of the first and second liposomes in step (a) independently comprises a hydrophilic core; and a lipid bilayer shell formed by a cholesterol, and one or more of a phospholipid optionally modified with a polyethylene glycol (PEG), in which the PEG-modified phospholipid is arranged in the manner that the PEG are disposed outside the lipid bilayer shell, and the PEG is at least 7% by weight based on the total weight of the first or second liposomes;
   the drug and the CT contrast agent are respectively disposed within the hydrophilic cores of the first and second liposomes; and
   an increase in the CEST signals respectively measured at about 1.2 ppm, 4.3 ppm, and −3.4 ppm in step (c) represent the presence of the PEG, the CT contrast agent, and the phospholipid bilayer of the first or second liposomes in the OB and FL regions.

2. The method of claim 1, wherein in step (a), the first and second liposomes are administered to the subject at a ratio of 1:1 by weight.

3. The method of claim 1, wherein the phospholipid is selected from the group consisting of ceramide phosphorylcholine, ceramide phosphorylethanolamine, ceramide phosphoryllipid, 1,2-Distearoyl-sn-glycero-3-phosphocholine (DSPC), 1,2-Dipalmitoyl-sn-glycero-3-phosphocholine (DPPC), 1,2-dioleoyl-sn-glycero-3-phosphocholine (DOPC), 1,2-Distearoyl-sn-glycero-3-phosphoglycerol (DSPG), 1,2-Dipalmitoyl-sn-glycero-3-phosphoglycerol (DPPG), 1,2-Dioleoyl-sn-glycero-3-phosphoethanolamine (DOPE), 1,2-Distearoyl-sn-glycero-3-phosphoethanolamine (DSPE) 1,2-dioleoyl-3-trimethylammonium propane (DOTAP), 1,2-distearoyl-3-trimethylammonium propane (DSTAP), 1,2-dimyristoyl glycerol (DMG), phosphatidylethanolamine (PE), phosphatidylcholine (PC), phosphatidylserine (PS), phosphatidylinositol (PI), and phosphatidylglycerol (PG).

4. The method of claim 3, wherein the DSPE is modified with the PEG, and the lipid bilayer shell is formed by the DSPC, the cholesterol, and the PEG-modified DSPE at a ratio of 50:40:10 by weight.

5. The method of claim 4, wherein the drug is selected from the group consisting of a protein, a peptide, a small molecule drug, an antibody, and a nucleic acid.

6. The method of claim 5, wherein the small molecule drug is an anti-cancer drug or a neurodegenerative drug.

7. The method of claim 6, wherein the anti-cancer drug is selected from the group consisting of cisplatin, carboplatin, oxaliplatin, cyclophosphamide, chlorambucil, ifosfamide, doxorubicin, daunorubicin, valrubicin, idarubicin, vincristine, vinblastine, taxol, docetaxel, camptothecin (CPT), irinotecan (CPT-11), and topotecan (TPT).

8. The method of claim 5, wherein the antibody is selected from the group consisting of imatinib, gefitinib, erlotinib, cetuximab, panitumumab, zalutumumab, nimotuzumab, and matuzumab.

9. The method of claim 6, wherein the neurodegenerative drug is selected from the group consisting of amantadine, apomorphine, baclofen, carbidopa, levodopa, dantrolene, donepezil, entacapone, galantamine, memantine, pramipexole, rasagiline, riluzole, rivastigmine, ropinirole, selegiline, tacrine, tetrabenazine, tizanidine, and tolcapone.

10. The method of claim 1, wherein the CT contrast agent is selected from the group consisting of iohexol, ioxaglic acid, metrizamide, iopamidol, iopromide, iotrolan, ioversol, iopentol, iodixanol, iomeprol, iobitidiol, and ioxilan.

11. The method of claim 10, wherein the CT contrast agent is iohexol.

12. The method of claim 1, wherein the first or second liposomes are independently in the form of a drop, a spray, a mist, or a mixture thereof suitable for applied to the nasal or sinus passages of the subject.

13. The method of claim 12, wherein the subject is a human.

* * * * *